(12) United States Patent
Collu et al.

(10) Patent No.: US 12,281,287 B2
(45) Date of Patent: *Apr. 22, 2025

(54) TREATMENT COMPOSITIONS COMPRISING CERTAIN PLANT ROSIN MATERIALS

(71) Applicant: The Procter & Gamble Company, Cincinnati, OH (US)

(72) Inventors: Mattia Collu, Saint-Gilles (BE); Cédric Marc Tahon, Oost-Vlaanderen (BE); Johan Smets, Lubbeek (BE)

(73) Assignee: The Procter & Gamble Company, Cincinnati, OH (US)

( * ) Notice: Subject to any disclaimer, the term of this patent is extended or adjusted under 35 U.S.C. 154(b) by 656 days.

This patent is subject to a terminal disclaimer.

(21) Appl. No.: 17/549,922

(22) Filed: Dec. 14, 2021

(65) Prior Publication Data

US 2022/0186149 A1 Jun. 16, 2022

(30) Foreign Application Priority Data

Dec. 16, 2020 (EP) .................................. 20214457

(51) Int. Cl.
| | | |
|---|---|---|
| *C11D 1/00* | (2006.01) | |
| *B08B 3/04* | (2006.01) | |
| *C11D 3/00* | (2006.01) | |
| *C11D 3/38* | (2006.01) | |
| *C11D 3/382* | (2006.01) | |
| *C11D 3/50* | (2006.01) | |

(52) U.S. Cl.
CPC ............ *C11D 3/382* (2013.01); *C11D 3/0015* (2013.01); *C11D 3/50* (2013.01)

(58) Field of Classification Search
CPC ....... C11D 1/00; C11D 3/0015; C11D 3/2065; C11D 3/2093; C11D 3/38; C11D 3/382; C11D 3/50; C11D 3/505; B08B 3/04
See application file for complete search history.

(56) References Cited

U.S. PATENT DOCUMENTS

| | | |
|---|---|---|
| 2,571,689 A | 10/1951 | Maria et al. |
| 2,776,276 A | 1/1957 | Glasebrook et al. |

(Continued)

FOREIGN PATENT DOCUMENTS

| | | |
|---|---|---|
| EP | 0138597 A2 | 4/1985 |
| EP | 1038910 A1 | 9/2000 |

(Continued)

OTHER PUBLICATIONS

Extended European Search Report and Search Opinion; Application No. 20214457.2 ; dated Feb. 7, 2021; 08 pages.

(Continued)

*Primary Examiner* — Brian P Mruk
(74) *Attorney, Agent, or Firm* — Carolyn S. Powell

(57) ABSTRACT

Treatment composition that include certain plant rosin materials and one or more benefit agents, for example fragrance materials, where the plant rosin materials are certain plant rosin esters and/or have certain characteristics, such as certain softening points, acid numbers, and/or color grades. Related methods of making and using such compositions.

21 Claims, 1 Drawing Sheet
(1 of 1 Drawing Sheet(s) Filed in Color)

(56) References Cited

U.S. PATENT DOCUMENTS

| | | | | |
|---|---|---|---|---|
| 3,950,510 | A | * | 4/1976 | Adams ................ A61K 8/922 |
| | | | | 510/432 |
| 5,362,715 | A | | 11/1994 | Cohen |
| 5,478,567 | A | | 12/1995 | Nakagawa et al. |
| 6,869,923 | B1 | | 3/2005 | Cunningham |
| 7,438,897 | B2 | | 10/2008 | Gupta |
| 7,795,476 | B2 | | 9/2010 | Corzani |
| 8,802,729 | B2 | | 8/2014 | Fenyvesi et al. |
| 9,186,642 | B2 | | 11/2015 | Dihora |
| 10,582,705 | B2 | | 3/2020 | Conover |
| 2002/0018760 | A1 | | 2/2002 | Vatter et al. |
| 2004/0121926 | A1 | | 6/2004 | Waits et al. |
| 2006/0020057 | A1 | | 1/2006 | Maas et al. |
| 2006/0154850 | A1 | | 7/2006 | Quellet |
| 2007/0129476 | A1 | | 6/2007 | Macbeath et al. |
| 2010/0089420 | A1 | | 4/2010 | Greenberg |
| 2013/0125297 | A1 | | 5/2013 | Pagani |
| 2019/0153354 | A1 | | 5/2019 | Lankin et al. |
| 2019/0373883 | A1 | * | 12/2019 | Conover ................ A01N 25/34 |

FOREIGN PATENT DOCUMENTS

| | | |
|---|---|---|
| GB | 1340043 A | 12/1973 |
| GB | 1349741 A | 4/1974 |
| GB | 1419116 A | 12/1975 |
| GB | 1515299 A | 6/1978 |
| IT | 202000004684 A1 | 9/2021 |
| JP | 2001262199 A | 9/2001 |
| WO | 2011030158 A2 | 3/2011 |
| WO | 2019051165 A1 | 3/2019 |
| WO | 2020058373 A1 | 3/2020 |
| WO | 2020234263 A1 | 11/2020 |

OTHER PUBLICATIONS

All Office Actions; U.S. Appl. No. 17/549,916, filed Dec. 14, 2021.
All Office Actions; U.S. Appl. No. 17/549,919, filed Dec. 14, 2021.
All Office Actions; U.S. Appl. No. 17/549,923, filed Dec. 14, 2021.
Glycerol ester of wood rosin INV, XP55811290 Retrieved from the Internet URL:https://en.wikipedia.org/wiki/Glycerol ester of wood rosin, dated Mar. 4, 2021, p. 2.
Database Gnpd Mintel,"Moist Diane Extra Moist & Shine Hair Mask has been relaunched", http:llwww.gnpd.com T, dated Jan. 29, 2020 pp. 3.
Eastman rosin products, "Natural resins for adhesion, wetting, viscocity control ", p. 08.
Mahmoud Abdul-Raheim,"BAOJ Chemistry Rosin Chemistry, Derivatives, and Applications a review", vol. 4, dated 2018, p. 2 of 16.
Polymer Properties Database, "Rosin Esters and Polymers", https://polymerdatabase.com/polymer classes/Rosin.html, dated 2015, p. 03.
Satish Kumar Gupta,"Rosin: A naturally derived excipient in drug delivery systems, Department of Pharmaceutical Technology", dated 2013, pp. 05.
U.S. Appl. No. 17/549,916, filed Dec. 14, 2021, to first inventor Mattia Collu et al.
U.S. Appl. No. 17/549,919, filed Dec. 14, 2021, to first inventor Mattia Collu et al.
U.S. Appl. No. 17/549,923, filed Dec. 14, 2021, to first inventor Mattia Collu et al.
PCT Search Report and Written Opinion for PCT/US2021/072890; dated May 23, 2022,15 pages.
Bambang Wiyono et al. "Chemical Compositions of Pine Resin, Rosin and Turpentine Oil from West Java", Journal of Forestry Research, vol. 3, No. 1, dated Mar. 1, 2016; pp. 7-17.
Database GNPD Mintel; "Foundation EX SPF 50+ PA++++", http://www.gnpd.com, dated May 2020; 5 Pages.
Database GNPD Mintel; "Hair Color Treatment", http://www.gnpd.com; dated Nov. 17, 2016; 4 Pages.
Database GNPD Mintel; "Light Luminous Hydrating Lipstik" http://www.gnpd.com; dated Jul. 1, 2020; 4 Pages.
Database GNPD Mintel; "Moisturizing Lip Balm", http;//www.gnpd.com, dated Nov. 10, 2020 , 3 Pages.
Database GNPD Mintel; "Shaving Oil", http://www.gnpd.com, dated May 2, 2018 , 5 Pages.
ESR—EP Search Report and Written Opinion; Application No. 21214390.3, dated May 30, 2022, 9 pages.

* cited by examiner

| Resin No. | LFE Product upon storage | Resin No. | LFE Product upon storage |
|---|---|---|---|
| 1 | 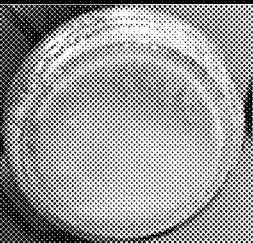 | 7 | 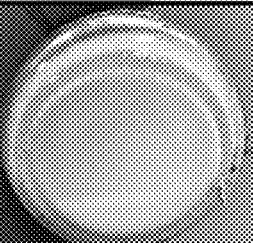 |
| 2 | 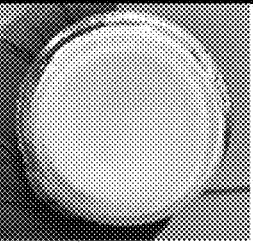 | 8 | 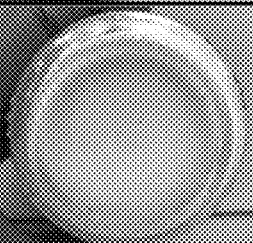 |
| 3 | 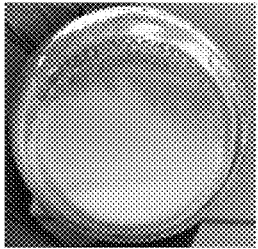 | 9 | 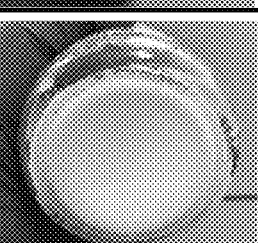 |
| 4 | 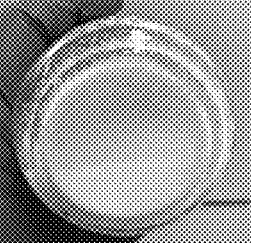 | 10 | 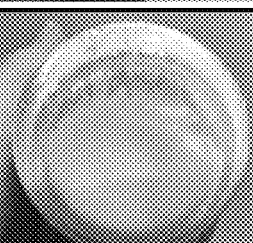 |
| 5 | 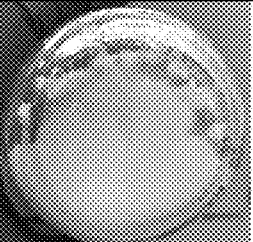 | 11 | 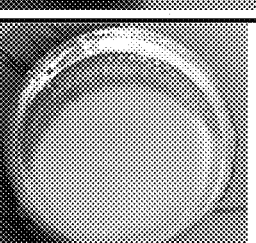 |
| 6 | 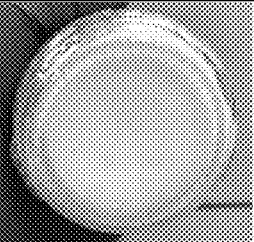 | | |

TREATMENT COMPOSITIONS COMPRISING CERTAIN PLANT ROSIN MATERIALS

FIELD OF THE INVENTION

The present disclosure relates to treatment composition that include certain plant rosin materials and one or more benefit agents, for example fragrance materials, where the plant rosin materials are certain plant rosin esters and/or have certain characteristics, such as certain softening points, acid numbers, and/or color grades. The present disclosure also relates to related methods of making and using such compositions.

BACKGROUND OF THE INVENTION

Manufacturers of treatment compositions, such as liquid fabric softeners, can employ various delivery systems to facilitate improved delivery of benefit agents. Such systems may take the form of core-shell particles and/or deposition aids, such as cationic polymers.

However, these delivery systems often require synthetic materials, which may not be preferred by today's environmentally-conscious consumer. Thus, the manufacturer is continuously seeking naturally derived materials that provide improved performance profiles.

Rosin-based materials derived from plants, typically pine trees, have been disclosed for being diluents, carriers, and fixatives in various consumer products. However, their use as delivery agents and/or performance enhancers has not been extensively explored. Additionally, some of these materials are difficult to process, or made lead to phase instabilities in a final product.

There is an ongoing need for treatment compositions that include naturally derived benefit agent delivery systems that provide improved performance and/or convenient processing.

SUMMARY OF THE INVENTION

The present disclosure relates to treatment compositions that include certain plant rosin materials.

For example, the present disclosure relates to treatment compositions that include a plant rosin material, where the plant rosin material is a plant rosin ester material, where the plant rosin ester material is derived from a plant rosin and an alcohol, the alcohol including (a) from two to six carbon atoms, and/or (b) from two to six hydroxyl groups, and where the treatment composition further includes one or more benefit agents, which may preferably include fragrance materials.

The present disclosure also relates to a treatment composition that includes a plant rosin material and one or more benefit agents, where the plant rosin material is a plant rosin ester material, and where the plant rosin ester material comprises, on average, from about two to about six moles of ester groups per mole of plant rosin ester material.

The present disclosure also relates to a treatment composition that includes a plant rosin material, where the plant rosin material is characterized by at least one, preferably at least two, preferably all three, of the following characteristics: (a) a softening point of from about 50° C. to about 120° C., preferably from about 60° C. to about 100° C.; (b) an acid number of from about 0 to about 100, preferably from about 0 to about 80, more preferably from about 0 to about 60, more preferably from about 0 to about 40, even more preferably from about 0 to about 20; and/or (c) a color grade of from about 1 to about 10, preferably from about 1 to about 8, more preferably from about 1 to about 6, as graded on the Gardner Color standard number scale; and where the treatment composition further includes one or more benefit agents.

The present disclosure also relates to a method of treating a surface, preferably a fabric, where the method includes the step of contacting the surface with the treatment composition as described herein, optionally in the presence of water.

BRIEF DESCRIPTION OF THE DRAWINGS

The patent or application file contains at least one photograph executed in color. Copies of this patent or patent application publication with color photograph(s) will be provided by the Office upon request and payment of the necessary fee.

The figures herein are illustrative in nature and are not intended to be limiting.

FIG. 1 shows color photographs of liquid fabric enhancer (LFE) products that include certain plant resin materials.

DETAILED DESCRIPTION OF THE INVENTION

The present disclosure relates to treatment compositions that include certain plant rosin materials and one or more benefit agents, such as perfume. As indicated in the name, plant rosin materials are derived from plants, typically from pine trees, and therefore are attractive as natural or sustainable materials, even if subsequently modified or derivatized.

It has been found that by selecting certain plant rosin materials that have particular chemistries and/or physical properties, the performance of the benefit agent is improved at certain touchpoints. Without being bound by theory, it is believed that specific type of rosins are preferred as they enable a good balance between building strong molecular interactions with certain benefit agents, such as perfume molecules, while ensuring satisfactory processability and product stability.

For example, it is believed that strong molecular interactions are important to facilitate good delivery efficiency of the benefit agent. The molecular interactions are based on the terpene structures present in the plant rosin itself; therefore, preferred resins have (or are chemically modified to have) a structure that favors molecular interactions that bind the rosin with the benefit agent. However, it is further believed that the molecular interaction with the benefit agent should not exceed a certain threshold, as high levels may cause difficulties in product-making processes, for example due to a plant rosin's high viscosity and low dispersibility in the finished product.

Therefore, preferred resins are the ones capable of building good molecular interaction with the delivery benefit, while at the same time allowing, for example, good dispersibility properties in the finished product formulation. For example, resins with low rosin acid content (evidenced by a relatively low acid number) may be preferred, as it is believed that they tend to exhibit good dispersibility properties. Additionally, rosin esters may be preferred, as it is believed that their three-dimensional structure facilitates a good ability to bind with the benefit agent. Furthermore, hydrogenated resin may also be preferred as they tend to exhibit resistance to oxidation.

The components, compositions, and processes of the present disclosure are described in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein "consumer product," means baby care, beauty care, fabric & home care, family care, feminine care, and/or health care products or devices intended to be used or consumed in the form in which it is sold, and not intended for subsequent commercial manufacture or modification. Such products include but are not limited to diapers, bibs, wipes; products for and/or methods relating to treating human hair, including bleaching, coloring, dyeing, conditioning, shampooing, styling; deodorants and antiperspirants; personal cleansing; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; adult incontinence products; products and/or methods relating to oral care including toothpastes, tooth gels, tooth rinses, denture adhesives, tooth whitening; over-the-counter health care including cough and cold remedies; pest control products; and water purification.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Treatment Composition

The present disclosure relates to treatment compositions that comprise certain plant rosin materials and one or more benefit agents. The treatment compositions may be useful for treating a surface, such as fabric, a hard surface, hair, and/or skin.

The treatment composition may be a consumer product composition. The consumer product composition may be a fabric care composition, a hard surface cleaner composition, a dish care composition, a hair care composition, a body cleansing composition, or a mixture thereof. The consumer product composition may be a conditioning composition, such as a liquid fabric enhancer composition or a hair conditioner composition.

The treatment compositions of the present disclosure may be fabric care compositions. Such compositions may be used as a pre-laundering treatment, a post-laundering treatment, or may be added during the rinse or wash cycle of the laundering operation. The fabric care composition may be a fabric detergent composition, a fabric conditioning composition, or a mixture thereof, preferably a fabric conditioning composition. Fabric conditioning compositions may include liquid fabric softeners and liquid fabric enhancing compositions.

The treatment composition may be in any suitable form, for example in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam/mousse, a non-woven sheet, or a mixture thereof, preferably a liquid.

The treatment composition may be in the form of a liquid. The liquid composition may include from about 30%, or from about 40%, or from about 50%, to about 99%, or to about 95%, or to about 90%, or to about 75%, or to about 70%, or to about 60%, by weight of the composition, of water. The liquid composition may be a liquid laundry detergent, a liquid fabric conditioner, a liquid dish detergent, a hair shampoo, a hair conditioner, or a mixture thereof.

The treatment composition may be in the form of a solid. The solid composition may be a powdered or granular composition. Such compositions may be agglomerated or spray-dried. Such composition may include a plurality of granules or particles, at least some of which include comprise different compositions. The composition may be a powdered or granular cleaning composition, which may include a bleaching agent. The composition may be in the form of a bead or pastille, which may be pastilled from a liquid melt. The composition may be an extruded product.

The treatment composition may be in the form of a unitized dose article, such as a tablet, a pouch, a sheet, or a fibrous article. Unitized dose articles in the form of pouches typically include a water-soluble film, such as a polyvinyl alcohol water-soluble film, that at least partially encapsulates a composition. Suitable films are available from Mono-Sol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof. Pouched compositions may have relatively low amounts of water, for example less than about 20%, or less than about 15%, or less than about 12%, or less than about 10%, or less than about 8%, by weight of the detergent composition, of water.

The treatment composition may be in the form of a spray and may be dispensed from a bottle, for example, via a trigger sprayer and/or an aerosol container with a valve.

When the treatment composition is a liquid, the composition may be characterized by a viscosity. The composition may have a viscosity of from about 1 to about 1500 centipoises (about 1-1500 mPa*s), from about 50 to about 1000 centipoises (about 50-1000 mPa*s), or from about 100 to 500 centipoises (about 100-500 mPa*s), or from about 100 to about 200 centipoises (about 100-200 mPa*s), at 20 $s^{-1}$ and 21° C., is disclosed. Relatively lower viscosities allow for improved dosing and/or less residue in a dispenser drawer. Viscosity is determined according to the method provided in the Test Methods section below.

The treatment compositions of the present disclosure may be characterized by a pH of from about 2 to about 12, or from about 2 to about 8.5, or from about 2 to about 7, or from about 2 to about 5. The treatment compositions of the present disclosure may have a pH of from about 2 to about 4, preferably a pH of from about 2 to about 3.7, more preferably a pH from about 2 to about 3.5, preferably in the form of an aqueous liquid. It is believed that such pH levels facilitate stability of certain adjuncts, such as conditioning actives (e.g., esterquats). The pH of a composition is determined by dissolving/dispersing the composition in deionized water to form a solution at 10% concentration, at about 20° C.

The plant rosin material and the one or more benefit agents may be present in a weight ratio of from about 5:95 to about 95:5, preferably from about 20:80 to about 80:20, more preferably from about 30:70 to about 70:30, more preferably from about 40:60 to about 60:40.

Plant Rosin Material

The treatment compositions and processes described herein contain plant rosin material. It is believed that by selecting particular plant rosin materials, such as those characterized by certain characteristics (e.g., softening point and/or acid number within a certain range), by certain chemistries (e.g., rosin esters), or by a combination thereof, the performance of a treatment composition may be improved.

As used herein, "plant rosin material" may include plant rosins (including resin acids), plant rosin derivatives, or mixtures thereof. Plant rosin material in the present compositions and processes can provide performance benefits, for example by facilitating improved deposition and/or stability of benefit agents. Such materials may further be preferred to known alternatives in the presently disclosed compositions and processes because they are derived from natural and/or sustainable resources.

As discussed in more detail below, plant rosin is typically derived from conifer plants (class: *Pinopsida*), usually from pine trees (genus: *Pinus*). Also called "colophony," plant rosin is a solid material produced by heating liquid resins to vaporize the volatile liquid terpene components. Plant rosins are typically composed of resin acids such as abietic acid and related compounds. Plant rosins may be further derivatized, for example through esterification and/or hydrogenation.

The compositions of the present disclosure may comprise from about 0.01% to about 10%, by weight of the composition, of plant rosin material. The compositions may comprise from about 0.01% to about 5%, or from about 0.05% to about 3%, or from about 0.1% to about 1%, by weight of the composition of plant rosin material.

Plant rosin materials may be characterized by a softening point. Plant rosin materials are typically solid at room temperature, but the softening point is a measure of the glass transition temperature associated with these materials. The softening point of a plant rosin material is determined according to method provided in the Test Method section below.

The plant rosin material may be characterized by a softening point of from about 50° C. to about 175° C., or from about 60° C. to about 150° C., or from about 75° C. to about 125° C. Preferred plant rosin materials may be characterized by a softening point of from about 50° C. to about 120° C., preferably from about 60° C. to about 100° C. Rosins may need to be softened by heating in order to be incorporated into consumer products. Thus, for ease of processing and/or energy savings, plant rosin materials having relatively lower softening points (e.g., less than 125° C.) may be preferred for the compositions and processes of the present disclosure. Lower softening points may also have an effect on improving the deposition aid performance of the plant rosin material.

Plant rosin materials may be characterized by an acid number (sometimes called "acid value"). The acid number of a plant rosin material relates to the total free acid content of these products. The acid number of a plant rosin material is determined according to method provided in the Test Method section below.

Plant rosin materials may be characterized by an acid number less than about 175, e.g., from about 0 to about 175. For the compositions and processes of the present disclosure, it may be preferred to use plant rosin material having a relatively low acid number, such as less than about 125, preferably less than about 100, more preferably less than about 75, even more preferably less than about 50, more preferably less than about 25, so as to have minimal effect on the final pH of the treatment composition. Preferred plant rosin materials may be characterized by an acid number of from about 0 to about 100, preferably from about 0 to about 80, more preferably from about 0 to about 60, more preferably from about 0 to about 40, even more preferably from about 0 to about 20. Without being bound by theory, it is believed that plant rosin materials having a relatively low acid number may also be more easily dispersible in the treatment compositions of the present disclosure.

That being said, plant rosin materials having a relatively high acid number (e.g., from about 125 to about 175, preferably from about 150 to about 175) can be useful, particularly if the plant rosin material also has a relatively low softening point (e.g., less than about 100° C., preferably less than about 80° C.), and even more so if the material is also at least partially hydrogenated.

The color of the plant rosin material may be graded based on the Gardner Color standard number, ranging 1 to 18. So as to have minimal effect on the final color of the treatment composition, preferred plant rosin materials of the present disclosure may have a color grade of from about 1 to about 10, preferably from about 1 to about 8, preferably from about 1 to about 6. The color grade of a plant rosin material is determined according to method provided in the Test Method section below.

The most preferred plant rosin materials tend to be characterized by a combination of the characteristics provided above. For example, the plant rosin material may be characterized by at least one, preferably at least two, preferably all three, of the following characteristics: (a) a softening point of from about 50° C. to about 120° C., preferably from about 60° C. to about 100° C.; (b) an acid number of from about 0 to about 100, preferably from about 0 to about 80, more preferably from about 0 to about 60; and/or (c) a color grade of from about 1 to about 10, preferably from about 1 to about 8, more preferably from about 1 to about 6, as graded on the Gardner Color standard number. In particular, the plant rosin material may be characterized by a softening point of from about 60° C. to about 100° C., and by an acid number of from about 0 to about 80, more preferably an acid number of from about 0 to about 60. It has been found that plant rosin materials having these characteristics are particularly effective at improving the performance of the associated benefit agent, such as perfume.

Plant rosin materials may have an odor. Naturally derived resins have an abundance of terpenic compounds. For the compositions and processes of the present disclosure, it may be preferred to select compound with a relatively low amount of terpenic structures and/or odor, so that the naturally derived resin will not interfere with the overall character perception. On the other hand, if there is a desire for a pine-tree-like fragrance character, then the presence of terpenic structures may be preferred.

For example, gum rosins may be preferred over tall oil rosins, as tall oil rosins may include sulfur contaminants that affect the odor. On the other hand, it may be desirable for the plant rosin materials to have a detectable odor, as the "piney" scent associated with rosin material may be useful or desirable in a particular product composition.

Plant rosin materials are typically relatively insoluble in water. For example, plant resin materials according to the present disclosure may be characterized by a solubility of less than 1 g/L, or less than 100 g/L, or less than 1 g/L, or less than 0.1 g/L, or less than about 0.01 g/L, in deionized water at 22° C. Without wishing to be bound by theory, it is believed that the relatively insoluble nature of the plant rosin materials of the present disclosure contribute to the deposition efficiency and performance of the associated benefit agent.

Plant rosin materials may be characterized by a density. Typically, the plant rosin materials are characterized by a density of greater than 1.0 kg/dm$^3$, preferably at least 1.1 kg/dm$^3$, at 25° C.

Plant rosin materials are typically flammable. For the compositions and processes of the present disclosure, it may be preferred to use plant rosin materials that have a relatively high flash point, e.g., higher than 190° C., to facilitate easier and safer processing. The flash point of a plant rosin material is determined according to method provided in the Test Method section below.

The treatment composition of the present disclosure may comprise particles, where the particles comprise the plant rosin material and the one or more benefit agents. Such particles may particularly effective to deliver the one or more benefit agent. The particles may be characterized by a volume-weighted mean particle size of from about 10 microns to about 400 microns, or from about 15 microns to about 300 microns, or from about 20 microns to about 250 microns, or from about 25 microns to about 200 microns, or from about 30 microns to about 150 microns, or from about 35 to about 125 microns, preferably from about 40 to about 100 microns, more preferably from about 50 to about 90 microns. A premix comprising the plant rosin material and the one or more benefit agents may be a particularly effective way to provide particles to a treatment composition. Volume-weighted average diameter is determined according to the method provided in the Test Method section below.

Plant rosins and plant rosin derivatives (such as rosin esters), as well as premixes comprising such substances, are discussed in more detail below.

A. Plant Rosins

The plant rosin material of the present disclosure may comprise a plant rosin. Plant rosin is typically obtainable from a plant's oleo-resin, which is may be exuded or otherwise derived from a pine tree. The oleo-resin may be distilled to remove volatile terpenes, and the solid material left behind is the plant rosin.

Plant rosin may be solid at room temperature. The solid rosin may be relatively translucent and/or glass-like. The plant rosin material may have a color ranging, for example from faint yellow to a darker brown color, or even black.

Plant rosin is typically a mixture of compounds and is primarily composed of resin acids (also called rosin acids). The plant rosin may comprise at least about 75%, or at least about 80%, or at least about 85%, or at least about 90%, or at least about 95%, by weight of the plant rosin, of resin acids. The plant rosin may comprise from about 75% to about 97%, or from about 80% to about 96%, or from about 85% to about 95%, or from about 90% to about 95%, by weight of the plant rosin, of resin acids. The remaining material may be non-acidic material.

Resin acids are typically monocarboxylic acids having three fused rings. Resin acids may be tricyclic diterpene monocarboxylic acids, for example with a molecular formula of $C_{19}H_{29}COOH$. Resin acids may include abietic-type acids, pimaric-type acids, plicatic acid, or mixtures thereof. The double bonds in abietic-type acids are typically conjugated, whereas the double bonds in pimaric-type acids are not typically conjugated.

Abietic-type acids may include abietic acid, neoabietic acid, dehydroabietic acid, palustric acid, levopimaric acid, or mixtures thereof. Pimaric-type acids may include pimaric acid, isopimaric acid, sandaracopimiaric acid, or mixtures thereof. Structures for these illustrative resin acids are provided below in Table A.

TABLE A

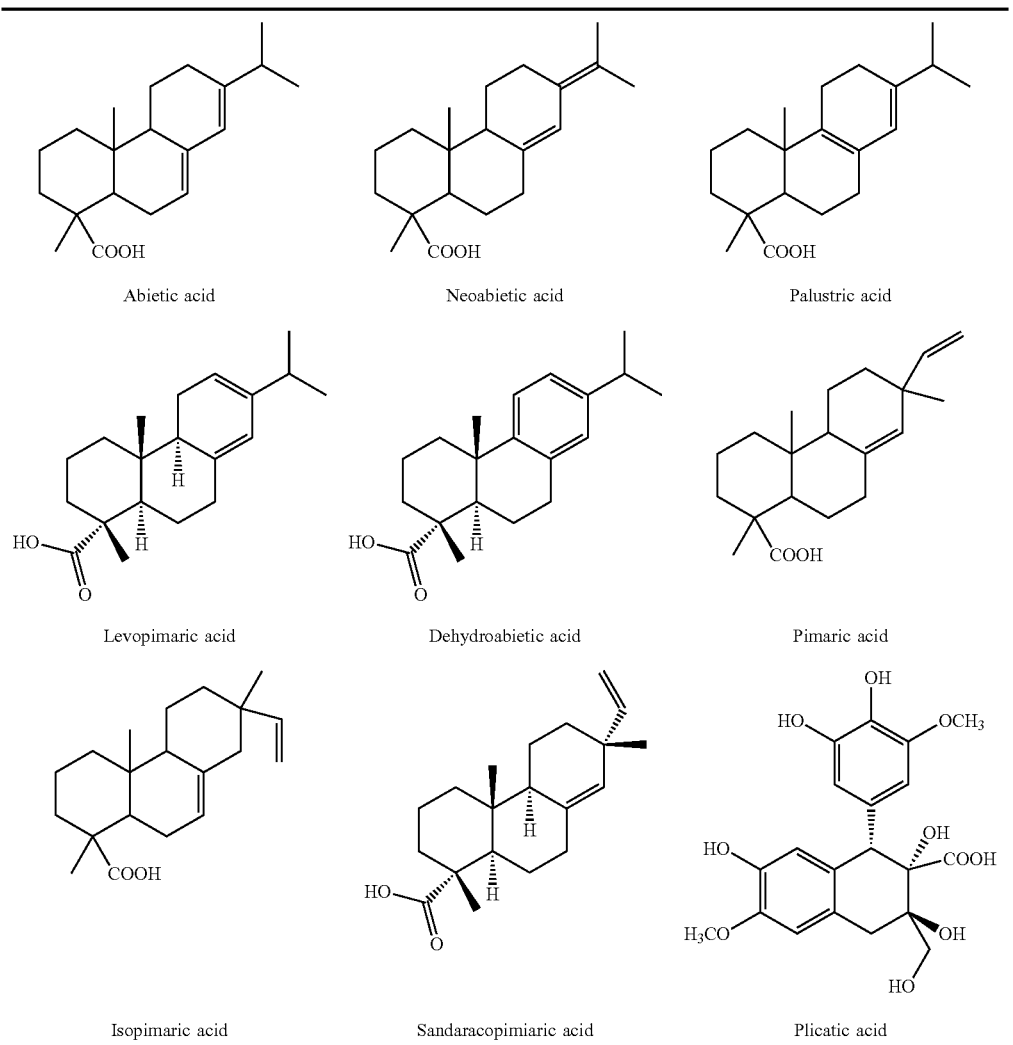

The plant rosin may comprise an abietic-type acid, preferably abietic acid. Abietic acid has the empirical formula $C_{19}H_{29}COOH$ and is also known as abietinic acid or sylvic acid. Abietic-type acids are typically the major component of a plant rosin. The plant rosin may comprise at least 50%, or at least 60%, or at least 70%, or at least 80%, or at least 85%, by weight of the plant rosin, of an abietic-type acid, preferably abietic acid.

Plant rosins may be classified depending on the source where it is obtained. For example, plant rosins of the present disclosure may be classified as (and may comprise) gum rosin, wood rosin, tall oil rosin, or a mixture thereof. Gum rosin may be derived from a resin extrudate of a tree or other plant and may be harvested by tapping or wounding the tree and then collecting and processing the extrudate. Wood rosin may be derived from materials that are harvested from pine tree stumps, for example through solvent extraction and/or distillation. Tall oil rosin is a by-product of the distillation of crude tall oil during the Kraft process of wood pulp manufacture when pulping pine trees.

Suitable plant rosins may be obtained, for example, from a variety of pine species, such as *Pinus massoniana* (Masson's pine), *P. elliotti* (slash pine), *P. palustris* (longleaf pine), *P. taeda* (loblolly pine), *P. oocarpa* (Mexican yellow pine), *P. leiophylla* (Chihuahua pine), *P. devoniana* (pino lacio, or Michoacan pine), *P. montezumae* (Montezuma pine), *P. pinaster* (maritime pine), *P. sylvestris* (Scots pine), *P. halepensis* (Aleppo pine), *P. insularis* (Benguet pine), *P. kesiya* (Khasi pine), *P. strobus* (Eastern white pine), or mixtures thereof.

B. Plant Rosin Ester

The plant rosin material of the present disclosure may comprise a plant rosin ester material (or simply "plant rosin ester" as used herein). Such materials may be made by chemically modifying a plant rosin material, such as a rosin acid like abietic acid, through an esterification process.

A plant rosin ester may be the reaction product of a plant rosin (e.g., a rosin acid) and an alcohol. A sample condensation reaction between three abietic acid molecules and one glycerol molecule is shown below, resulting in a rosin ester.

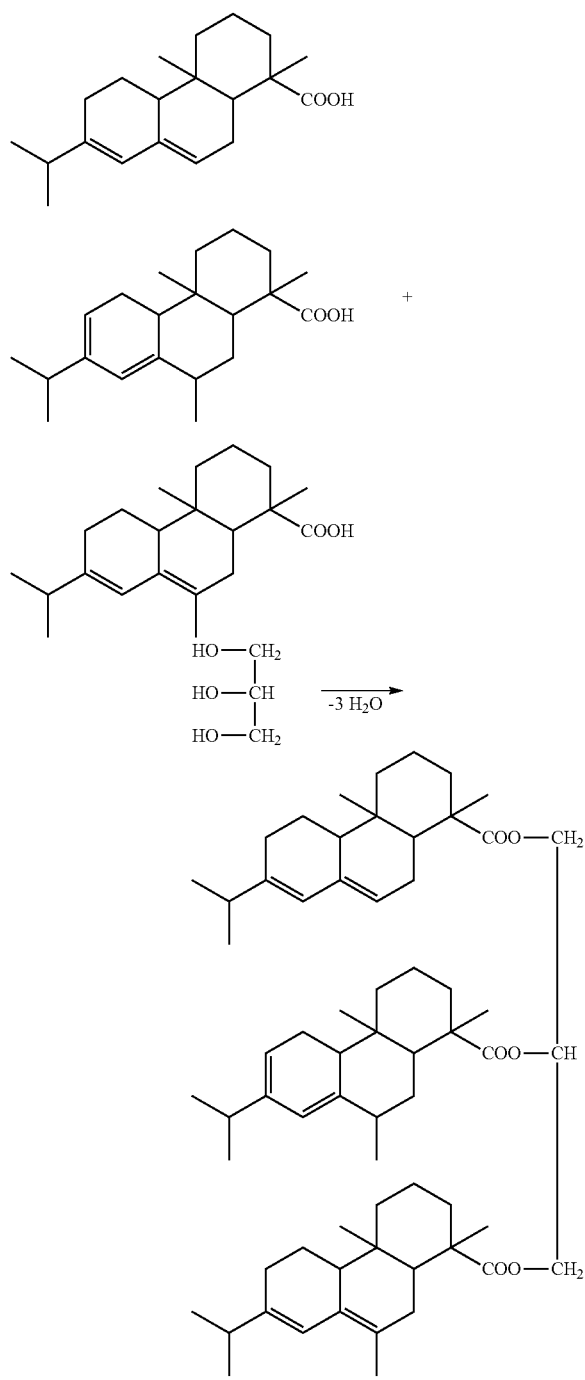

The plant rosin ester material may be derived from a plant rosin and an alcohol, where the alcohol comprises: (a) from two to six carbon atoms, and/or (b) from two to six hydroxyl groups.

Preferably, the alcohol will comprise more than one hydroxyl group and more than one carbon atom, as rosin esters formed from such alcohols believed to perform better than those with one ester group and/or one carbon (e.g., methyl esters). The alcohol may comprise (a) from two to six carbon atoms, and (b) from two to six hydroxyl groups. The alcohol from which the plant rosin ester material is derived may preferably comprise from two to five hydroxyl groups, more preferably from three to five hydroxyl groups, more preferably from three to four hydroxyl groups. The alcohol from which the plant rosin ester material is derived may comprise from two to five carbon atoms, more preferably from three to five carbon atoms. The alcohol from which the plant rosin ester material is derived may be selected from the group consisting of glycerol, pentaerythritol, and mixtures thereof, preferably glycerol.

The alcohol used in the esterification reaction may have a relatively low molecular weight. For example, the alcohol may have a molecular weight of from about to about 32 daltons to about 300 daltons, preferably from about 32 daltons to about 200 daltons, more preferably from about 32 daltons to about 150 daltons, even more preferably from about 90 daltons to about 150 daltons. Without wishing to be bound by theory, it is believed that a rosin ester formed from a lower-molecular-weight alcohol is likely to be characterized by a relatively lower softening point and/or a lower acid value compared to a rosin ester formed from a relatively higher-molecular-weight alcohol, thereby leading to better processability and/or performance.

The plant rosin ester material may comprise, on average, from about two to about six moles of ester groups per mole of plant rosin ester material.

The alcohol used in the esterification reaction may be glycerol or pentaerythritol. Thus, the plant rosin ester material may be a glyceryl rosin ester, a pentaerythrityl rosin ester, or a mixture thereof.

The plant rosin ester material may be characterized by one or more, preferably two or more, more preferably all three, of the following: (a) a softening point of from about 50° C. to about 120° C., preferably from about 60° C. to about 100° C.; and/or (b) an acid number of from about 0 to about 100, preferably from about 0 to about 80, more preferably from about 0 to about 60; and/or (c) a color grade of from about 1 to about 10, preferably from about 1 to about 8, more preferably from about 1 to about 6, as graded on the Gardner Color standard number.

The plant rosin ester material may be derived from gum rosin, wood rosin, and/or tall oil rosin, preferably gum rosin. The plant rosin ester material may comprise a gum rosin ester.

The plant rosin ester material may be at least partially hydrogenated.

C. Other Plant Rosin Derivatives

The plant rosin material may comprise other plant rosin derivatives in addition to, or as an alternative to, plant rosin esters. In some cases, the plant rosin esters may be further derivatized. Such derivatives may be produced by processes such as hydrogenation, dimerization, polymerization, saponification, or mixtures thereof.

The plant rosin material may comprise a hydrogenated rosin. Given that many plant rosin compounds (e.g., rosin acids) are unsaturated, they tend to be oxidatively unstable and may undergo color changes upon storage. Hydrogenation can help to stabilize the rosins and reduce undesirable color change. Furthermore, hydrogenated rosins tend to have lighter colors than the parent rosin, providing more formulation and aesthetic flexibility.

The plant rosins and/or rosin acids may be partially or fully hydrogenated. Below is a sample reaction for the partial and full hydrogenation of abietic acid.

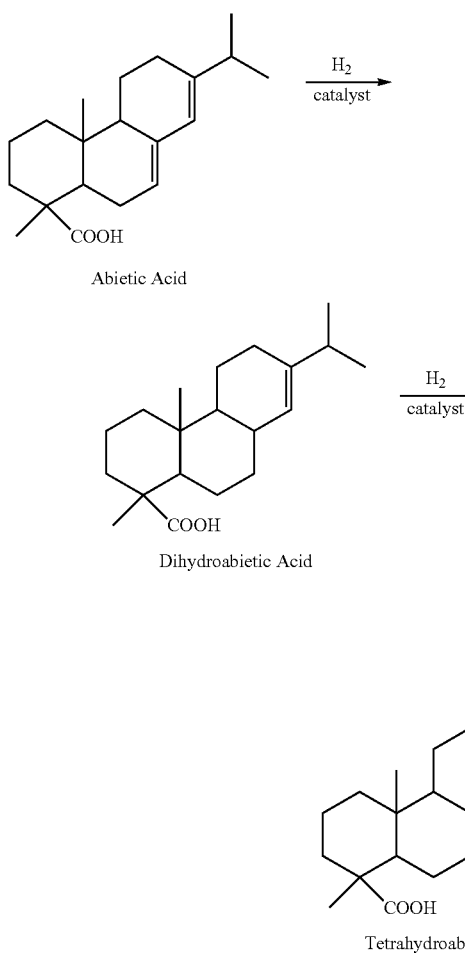

Abietic Acid

Dihydroabietic Acid

Tetrahydroabietic Acid

The treatment composition may comprise a plant rosin material is at least partially hydrogenated, preferably fully hydrogenated.

The plant rosin derivative may be both hydrogenated and esterified. For example, the plant rosin derivative may be a hydrogenated glyceryl ester.

The plant rosin material may comprise a dimerized plant rosin. Dimerization may be useful for increasing the softening point and/or stability of a rosin acid. A sample dimerization reaction of abietic acid is shown below.

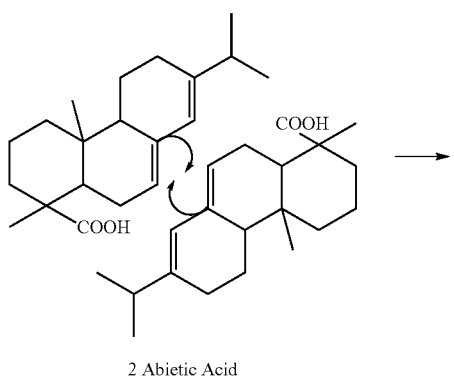

2 Abietic Acid

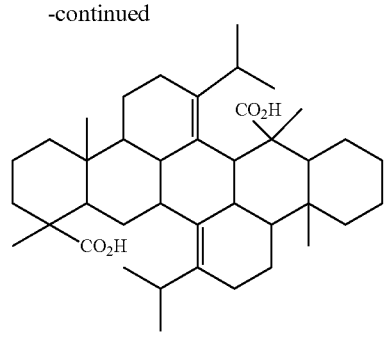

ROSIN ACID DIMER

As it is difficult or even impossible to completely dimerize a sample of rosins, rosin dimers are often present with undimerized rosin acids. Dimerized rosin acids may be further esterified.

A plant rosin derivative may dimerized through ions such as $Zi^{2+}$ or $Ca^{2+}$. For example, zinc resinates are plant rosin derivatives where two abietic acid compounds are bound to a zinc ion.

The plant rosin material may comprise a rosin-based polymer. As used here, in rosin-based polymer is intended to include compounds comprising rosin-based oligomers, including three or more monomeric units derived from rosin acids. The polymer may be a main-chain polymer or a side-chain polymer.

The plant rosin material may comprise a rosin soap, where a rosin acid is reacted with an alkali metal hydroxide (e.g., NaOH or KOH) or an alkaline earth metal hydroxide (e.g., $Ca(OH)_2$). More broadly, the plant rosin derivative may be the salt of a rosin acid.

The plant rosin material may comprise a functionalized plant rosin. In other word, the plant rosin may be functionalized, where one or more functional groups are added to the plant rosin.

A plant rosin material may include the product of a Diels-Alder reaction, such as the reaction product of a rosin acid and maleic anhydride; such reaction products may be polymerized.

A plant rosin material may include phenolic rosins, where a rosin is reacted with a phenol. A plant rosin derivative may include a rosin alcohol, wherein one or more of the carboxyl groups of the rosin acid are converted to hydroxyl groups.

Benefit Agent

In addition to the plant rosin material, the treatment compositions of the present disclosure comprise one or more benefit agents. It is believed that the particularly selected plant rosin materials as described above can lead to improved stability, delivery, and/or performance of the benefit agent on a target surface, such as a fabric or hard surface.

The compositions of the present disclosure may include the benefit agent at a level at which the benefit agent provides its intended benefit when the composition is used as intended. For example, the benefit agent may be present at a level of from about 0.05% to about 10%, or from about 0.05% to about 5%, or from about 0.1% to about 4%, by weight of the composition.

The benefit agent may be selected from the group consisting of fragrance material, silicone oils, waxes, hydrocarbons, higher fatty acids, essential oils, lipids, skin coolants, vitamins, sunscreens, antioxidants, glycerine, malodor reducing agents, odor-controlling materials, antistatic agents, softening agents, insect and moth repelling agents, colorants, optical brighteners, whiteness enhancers, defoamers, anti-foaming agents, UV protection agents for fabrics and skin, sun fade inhibitors, anti-allergenic agents, water proofing agents, skin care agents, glycerin, natural actives, aloe vera, vitamin E, shea butter, cocoa butter, brighteners, antiperspirant actives, emollients, skin sensates, and mixtures thereof. Particularly preferred benefit agents include fragrance materials.

The delivery efficacy of the benefit agent may be most efficacious when the benefit agent is relatively hydrophobic.

The benefit agent of the particles may include fragrance material (or "perfume" herein), which may comprise one or more perfume raw materials. The term "perfume raw material" (or "PRM") as used herein refers to compounds having a molecular weight of at least about 100 g/mol and which are useful in imparting an odor, fragrance, essence, or scent, either alone or with other perfume raw materials. Typical PRMs comprise inter alia alcohols, ketones, aldehydes, esters, ethers, nitrites, and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

Suitable perfume raw materials may include materials such as geraniol, linalool, linalyl acetate, pyranol, geranyl acetate, anisaldehyde, citral, citronellal, lysmeral, citronellol, rose oxide, tetrahydrolinalool, hydroxycitronellal, betaionone, menthol, cinnamaldehyde, anethole, vanillin, ethyl vanillin, eugenol, cinnamon oil, carvone, piperonal, and mixtures thereof. The perfume raw materials may include naturally derived materials, such as essential oils.

The PRMs may be characterized by their boiling points (B.P.) measured at the normal pressure (760 mm Hg), and their octanol/water partitioning coefficient (P), which may be described in terms of log P, determined according to the test method below. Based on these characteristics, the PRMs may be categorized as Quadrant I, Quadrant II, Quadrant III, or Quadrant IV perfumes, as described in more detail below. A perfume having a variety of PRMs from different quadrants may be desirable, for example, to provide fragrance benefits at different touchpoints during normal usage.

The perfume raw materials may comprise a perfume raw material selected from the group consisting of perfume raw materials having a boiling point (B.P.) lower than about 250° C. and a Log P lower than about 3, perfume raw materials having a B.P. of greater than about 250° C. and a Log P of greater than about 3, perfume raw materials having a B.P. of greater than about 250° C. and a Log P lower than about 3, perfume raw materials having a B.P. lower than about 250° C. and a Log P greater than about 3 and mixtures thereof. Perfume raw materials having a boiling point B.P. lower than about 250° C. and a Log P lower than about 3 are known as Quadrant I perfume raw materials. Quadrant 1 perfume raw materials are preferably limited to less than 30% of the perfume composition. Perfume raw materials having a B.P. of greater than about 250° C. and a Log P of greater than about 3 are known as Quadrant IV perfume raw materials, perfume raw materials having a B.P. of greater than about 250° C. and a Log P lower than about 3 are known as Quadrant II perfume raw materials, perfume raw materials having a B.P. lower than about 250° C. and a Log P greater than about 3 are known as a Quadrant III perfume raw materials. Suitable Quadrant I, II, III and IV perfume raw materials are disclosed in U.S. Pat. No. 6,869,923 B1.

The treatment composition may comprise fragrance material, where the fragrance material comprises from about 1% to about 40%, by weight of the fragrance material, of Quadrant I perfume raw materials, and/or from about 60% to about 99%, by weight of the fragrance material, of non-Quadrant I perfume raw materials.

The hydrophobic perfume raw materials may be characterized by a relatively high log P value, for example a log P of greater than about 3.0, and may include what is described above as Quadrant III PRMs, Quadrant IV PRMs, or mixtures thereof. The benefit agent may comprise at least about 50%, or at least about 60%, or at least about 70%, or at least about 80%, or at least about 90%, or about 100%, by weight of the benefit agent, of Quadrant III PRMs, Quadrant IV PRMs, or mixtures thereof. Compositions that comprise such levels of Quadrant III and/or IV PRMs as the benefit agent of the particles may be aqueous and comprise at least 60%, or at least 70%, or at least 80%, or at least 90%, or at least 95%, or at least 97%, by weight of the composition, of water, and/or less than 10%, or less than 5%, or less than 3%, surfactant.

Non-limiting examples of Quadrant III PRMs include iso-bornyl acetate, carvacrol, alpha-citronellol, paracymene, dihydro myrcenol, geranyl acetate, d-limonene, linalyl acetate, vertenex, and mixtures thereof.

Non-limiting examples of Quadrant IV (or enduring) PRMs include allyl cyclohexane propionate, ambrettolide, amyl benzoate, amyl cinnamate, amyl cinnamic aldehyde, amyl cinnamic aldehyde dimethyl acetal, iso-amyl salicylate, hydroxycitronellal-methyl anthranilate (known as Aurantiol®), benzophenone, benzyl salicylate, para-tert-butyl cyclohexyl acetate, iso-butyl quinoline, beta-caryophyllene, cadinene, cedrol, cedryl acetate, cedryl formate, cinnamyl cinnamate, cyclohexyl salicylate, cyclamen aldehyde, dihydro isojasmonate, diphenyl methane, diphenyl oxide, dodecalactone, 1-(1,2,3,4,5,6,7,8-octahydro-2,3,8,8-tetramethyl-2-naphthalenyl)-ethanone (known as iso E Super®), ethylene brassylate, methyl phenyl glycidate, ethyl undecylenate, 15-hydroxypentadecanoic acid lactone (known as Exaltolide®), 1,3,4,6,7,8-hexahydro-4,6,6,7,8,8-hexamethyl-cyclopenta-gamma-2-benzopyran (known as Galaxolide®), geranyl anthranilate, geranyl phenyl acetate, hexadecanolide, hexenyl salicylate, hexyl cinnamic aldehyde, hexyl salicylate, alpha-irone, gamma-ionone, gamma-n-methyl ionone, para-tertiary-butyl-alpha-methyl hydrocinnamic aldehyde (known as Lilial®), lilial (p-t-bucinal)®, linalyl benzoate, 2-methoxy naphthalene, methyl dihydrojasmone, musk indanone, musk ketone, musk tibetine, myristicin, oxahexadecanolide-10, oxahexadecanolide-11, patchouli alcohol, 5-acetyl-1,1,2,3,3,6-hexamethylindan (known as Phantolide®), phenyl ethyl benzoate, phenylethylphenylacetate, phenyl heptanol, phenyl hexanol, alpha-santalol, delta-undecalactone, gamma-undecalactone, vetiveryl acetate, yara-yara, ylangene, and mixtures thereof.

The one or more benefit agents may be combined with the plant rosin material in a premix, which may be added to a base composition to make the treatment compositions of the present disclosure. The base composition may comprise an adjunct ingredient, as described in more detail below. Thus, the treatment composition of the present disclosure may comprise a premix, where the premix comprises plant rosin material and one or more benefit agents. The treatment may be formed by a process comprising adding a premix to a base composition, where the premix comprises the plant rosin material and the one or more benefit agents, and where the base composition comprises the adjunct ingredient.

The premix may comprise from about 1% to about 99%, by weight of the premix, of the plant rosin material. The premix may comprise from about 1% to about 99%, by weight of the premix, of the benefit agent. The premix may comprise the plant rosin material and the benefit agent in a weight ratio of from about 1:99 to about 99:1, preferably from about 5:95 to about 95:5, more preferably from about 10:90 to about 90:10, more preferably from about 20:80 to about 80:20, more preferably from about 30:70 to about 80:20, more preferably from about 40:60 to about 80:20. It is believed that the performance benefit increases with higher plant rosin:benefit agent weight ratios.

The premix may comprise an emulsifying agent. The premix may comprise from about 1% to about 95%, or from about 5% to about 95%, preferably from about 5% to about 40% by weight of the premix, of the emulsifying agent. The premix may comprise the plant rosin material and the emulsifying agent in a weight ratio of from about 5:95 to about 95:5. The premix may comprise the benefit agent and the emulsifying agent in a weight ratio of from about 5:95 to about 95:5. Suitable emulsifying agents may include surfactants, amphiphilic polymers, or mixtures thereof.

Suitable surfactants may include nonionic surfactants, anionic surfactants, or mixtures thereof, preferably nonionic surfactants. Suitable nonionic surfactants may include alkoxylated surfactants, pyrrolidone-based surfactants (including alkyl pyrrolidones, preferably C12-alkyl pyrrolidones), alkyl polyglycosides, and mixture thereof. Preferable HLB value of the nonionic surfactant is from 3 to 12.5. Suitable commercially available nonionic surfactants may include Lutensol™ XP 40 (ex BASF), Lutensol™ XP 70 (ex BASF), Plurafac™ LF 224 (BASF), Plurafac™ LF 401 (BASF), Ecosurf™ EH 9 (DOW), Neodol™ surfactant (SHELL), Dobanol™ surfactants (SHELL), Surfadone™ LP-300 (ASHLAND, Planteren™ APG 600, or mixtures thereof.

Suitable amphiphilic polymers may include graft copolymers, such as poly(ethylene glycol)-poly(vinyl acetate) graft copolymer, polyvinyl caprolactam-polyvinyl acetate-polyethylene glycol graft copolymer, or mixtures thereof. Commercially available graft copolymers may include Sokalon® HP 22 or Soluplus®, both available from BASF.

The premix may be made by heating the plant rosin material. The plant rosin material may be heated to a temperature equal to or greater than the softening point of the plant rosin material. The premix may be made by combining the heated plant rosin material with the benefit agent, and mixing.

In order to favor the homogeneity of the premix, the mixing may take place in a heated oil bath set at a temperature equal to the softening point of the plant rosin material. As the samples become homogenous, the temperature can be progressively reduced, which helps to lower the risk of loss of volatile materials (e.g., evaporation of volatile PRMs).

A processing aid, for example an emulsifying agent as described above, can be added at any suitable point. Preferably, the emulsifying agent, if any, is combined with the plant rosin material prior to adding the benefit agent (e.g., perfume). It is believed that this order of addition improves the ease of homogenization of the mixture.

As an additional or alternative step to heating, the plant rosin material may be grinded to small particles and mixed with the benefit agent.

Once made, the premix may be stored at ambient temperatures. That being said, when using the premix to make a final product composition, the premix may be heated, for example heated to around 60° C., before being injected in the finished product or otherwise combined with a base composition. This heating step is most likely to be helpful when the premix is characterized by a relatively high rosin:benefit agent (e.g. perfume) weight ratio, such as greater than 50:50. When the premix comprises a nonionic surfactant, for example as an emulsifying agent, the heating step may not be required.

Adjunct Ingredients

The treatment compositions of the present disclosure may further include an adjunct ingredient in addition to the plant rosin materials and one or more benefit agents described above The base composition may comprise the adjunct ingredient, and adjunct ingredients may be added to the base composition before, during, and/or after the premix (as described above) is combined with the base compositions. The adjunct ingredient(s) may be suitable for delivering a treatment benefit to a target surface, such as a fabric or other textile. Adjuncts ingredients, as used herein, may also include agents that facilitate chemical or physical stability in the treatment compositions, such as buffers, structurants/thickeners, and/or carriers.

The adjunct ingredient(s) may be present in the composition at levels suitable for the intended use of the composition. Typical usage levels range from as low as 0.001% by weight of composition for adjuncts such as optical brighteners to 50% by weight of composition for builders.

The adjunct ingredient may include an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, a perfume delivery system, structure elasticizing agents, fabric softeners, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof. The compositions of the present disclosure may include, among other things, an amine, a surfactant system, a conditioning agent, a water-binding agent, a sulfite, a structurant, organic solvent, free perfume, a perfume delivery system, or mixtures thereof. Several of these adjuncts are described in more detail below.

The adjunct ingredient may comprise a surfactant system, conditioning actives, or combinations thereof. Preferably, the surfactant system comprises anionic surfactant, nonionic surfactant, cationic surfactant, and/or zwitterionic surfactant. Preferably, the fabric softening agents comprise a quaternary ammonium compound, silicone compounds, or both.

Liquid consumer product compositions according to the present disclosure may include a surfactant system. The surfactant system may consist of one type of surfactant. The surfactant system may include more than one surfactant.

The compositions of the present disclosure may include from about 20% to about 75%, or from about 25% to about 70%, or from about 30% to about 50%, by weight of the composition, of a surfactant system. Compositions of the present disclosure may include less than 20%, or less than 10%, or less than 5%, or less than 3%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES) including sodium laureth sulfate (SLES), alkyl sulfates (AS) including sodium lauryl sulfate (SLS), or mixtures thereof. Other suitable anionic surfactants include branched modified alkyl benzene sulfonates (MLAS), methyl ester sulfonates (MES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine). In certain treatment compositions, for example, those that include a cationic material such as a fabric conditioning agent, it may be desirable to limit the amount of anionic surfactant present; for example, the treatment composition may comprise less than 5%, or less than 3%, or less than 1%, or less than 0.1%, or even 0%, by weight of the treatment composition, of anionic surfactant.

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branhed alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

The compositions of the present disclosure may include a conditioning active. Compositions that contain conditioning actives may provide softness, anti-wrinkle, anti-static, conditioning, anti-stretch, color, and/or appearance benefits. Conditioning actives suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof. Preferably, the treatment composition comprises a conditioning active that comprises a quaternary ammonium ester compound, more preferably a quaternary ammonium ester compound in combination with a silicone.

Conditioning actives may be present at a level of from about 1% to about 99%, by weight of the composition. The composition may include from about 1%, or from about 2%, or from about 3%, to about 99%, or to about 75%, or to about 50%, or to about 40%, or to about 35%, or to about 30%, or to about 25%, or to about 20%, or to about 15%, or to about 10%, by weight of the composition, of conditioning active. The composition may include from about 5% to about 30%, by weight of the composition, of conditioning active.

Liquid treatment compositions according to the present disclosure may include an external structurant. External structurants can provide physical stability to liquid compositions according to the present disclosure, for example by helping to suspend particles. Structurants, when present, are preferably present in an effective amount that is capable of suspending particles in the treatment composition. External structurants may include non-polymeric crystalline, hydroxy-functional structurants and/or polymeric structurants.

Non-polymeric crystalline, hydroxyl functional structurants may comprise a crystallizable glyceride, which may be pre-emulsified to aid dispersion into the final detergent composition. Suitable crystallizable glycerides include hydrogenated castor oil or "HCO" or derivatives thereof, provided that it is capable of crystallizing in the liquid detergent composition.

Polymeric structurants may include naturally derived structurants and/or synthetic structurants. Naturally derived polymeric structurants include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. The structurant may comprise cellulosic fibers, for example in the form of microfibrillated cellulose. Cellulose may be derived from bacterial, wood, or other plants such as fruit or sugar beet.

Synthetic polymeric structurants include: polycarboxylates, polyacrylates, hydrophobically modified ethoxylated urethanes, hydrophobically modified non-ionic polyols and mixtures thereof. The polycarboxylate polymer may be a polyacrylate, polymethacrylate or mixtures thereof. The polyacrylate may be a copolymer of unsaturated mono- or di-carbonic acid and $C_1$-$C_{30}$ alkyl ester of the (meth)acrylic acid. Such copolymers are available from Lubrizol Corp. under the tradename Carbopol® Aqua 30.

The compositions of the present disclosure may include solvent, preferably organic solvent, such as a non-aminofunctional organic solvent. Suitable organic solvents may include glycerol, ethylene glycol, 1,3 propanediol, 1,2 propanediol, tetramethylene glycol, pentamethylene glycol, hexamethylene glycol, 2,3-butane diol, 1,3 butanediol, diethylene glycol, triethylene glycol, polyethylene glycol, glycerol formal dipropylene glycol, polypropylene glycol, dipropylene glycol n-butyl ether, and mixtures thereof. Organic solvents can provide physical stability benefits, particularly in compact formulations having relatively low water levels. The compositions of the present disclosure may include from about 5% to about 80%, or from about 10% to about 50%, by weight of the composition, of organic solvent.

Treatment compositions according to the present disclosure may include a perfume delivery system. Suitable perfume delivery systems may include core-shell encapsulates, pro-perfumes (such as amine- and/or silicone-based pro-perfumes), and mixtures thereof. Core-shell encapsulates may comprise a core and a shell surrounding the core. The core may comprise a benefit agent such as perfume, and optionally a partitioning modifier such as isopropyl myristate. The shell may comprise a polymer, for example melamine formaldehyde, polyurea, polyvinyl alcohol, polyacrylate, or a polysaccharide. Encapsulates may comprise a coating that can help with deposition, such as a coating comprising a cationic polymer. Suitable encapsulates may be characterized by a volume-weighted median particle size of from about 10 microns to about 100 microns, or from about 10 microns to about 50 microns, or from about 15 microns to about 40 microns. Perfume delivery systems may provide benefits such as improved perfume stability, deposition, and/or longevity, and may be particularly useful for perfume raw materials that do not associate well with the plant rosin materials of the present disclosure.

The compositions of the present disclosure may include additional aesthetic agents, such as those selected from dyes, opacifiers, pearlescent agents, or mixtures thereof.

Process of Making

The present disclosure also relates to processes for making treatment compositions, preferably liquid treatment compositions. The process of making a treatment composition, which may be a consumer product composition, may comprise the step of combining the ingredients (e.g., a plant rosin material, one or more benefit agents, and optionally an adjunct ingredient) as described herein.

The process of making a treatment composition, which may be a liquid, according to the present disclosure may comprise the steps of combining the plant rosin material and the one or more benefit agents as separate ingredients (e.g., without premixing the plant rosin material and the one or more benefit agents) with a liquid base composition, where the liquid base composition comprises an adjunct ingredient.

The process of making a liquid treatment composition according to the present disclosure may include the step of providing a premix. The premix may comprise the plant rosin material and the one or more benefit agents. The premix may be combined with a base composition, preferably a liquid base composition. The liquid base composition may comprise the adjunct ingredient.

The liquid treatment compositions of the present disclosure can be formulated into any suitable form and prepared by any process chosen by the formulator. The materials may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders.

The liquid treatment composition may be encapsulated in water-soluble film(s) according to known methods to form a unitized dose article.

The liquid treatment composition may be placed into an aerosol or other spray container according to known methods.

Process of Treating a Surface

The present disclosure also relates to a process of treating a surface, such as a fabric, a hard surface, hair, and/or skin. The process may include the step of contacting a surface with a treatment composition according to the present disclosure.

The contacting step may occur in the presence of water. The processes of the present disclosure may include diluting the compact liquid detergent composition with water to form a treatment liquor, which may contact the surface to be treated. The compact liquid detergent composition may be diluted from 100-fold to 1000-fold, or from 200-fold to 900-fold, or from 300-fold to 800-fold, by water.

The contacting step may occur in the drum of an automatic washing machine. The contacting step may occur as a pretreatment step.

Combinations

Specifically contemplated combinations of the disclosure are herein described in the following lettered paragraphs. These combinations are intended to be illustrative in nature and are not intended to be limiting.

A. A treatment composition comprising: a plant rosin material, wherein the plant rosin material is a plant rosin ester material, wherein the plant rosin ester material is derived from a plant rosin and an alcohol, the alcohol comprising: (a) from two to six carbon atoms, and/or (b) from two to six hydroxyl groups; the treatment composition further comprising one or more benefit agents.

B. A treatment composition comprising a plant rosin material and one or more benefit agents, wherein the plant rosin material is a plant rosin ester material, wherein the plant rosin ester material comprises, on average, from about two to about six moles of ester groups per mole of plant rosin ester material.

C. The treatment composition according paragraph B, wherein the plant rosin ester material is derived from a plant rosin and an alcohol, wherein the alcohol comprises from two to six carbon atoms.

D. The treatment composition according to any of paragraphs A-C, wherein the alcohol from which the plant rosin ester material is derived comprises from two to five carbon atoms, more preferably from three to five carbon atoms.

E. The treatment composition according to any of paragraphs A-D, wherein the alcohol from which the plant rosin ester material is derived comprises from two to five hydroxyl groups, more preferably from three to five hydroxyl groups, more preferably from three to four hydroxyl groups.

F. The treatment composition according to any of paragraphs A-E, wherein the alcohol from which the plant rosin ester material is derived is selected from the group consisting of glycerol, pentaerythritol, and mixtures thereof, preferably glycerol.

G. The treatment composition according to any of paragraphs A-F, wherein the plant rosin ester material is characterized by one or more of the following: a) a softening point of from about 50° C. to about 120° C., preferably from about 60° C. to about 100° C.; and/or b) an acid number of from about 0 to about 100, preferably from about 0 to about 80, more preferably from about 0 to about 60, more preferably from about 0 to about 40, even more preferably from about 0 to about 20; and/or c) a color grade of from about 1 to about 10, preferably from about 1 to about 8, more preferably from about 1 to about 6, as graded on the Gardner Color standard number.

H. A treatment composition comprising: a plant rosin material, wherein the plant rosin material is characterized by at least one, preferably at least two, preferably all three, of the following characteristics: a) a softening point of from about 50° C. to about 120° C., preferably from about 60° C. to about 100° C.; b) an acid number of from about 0 to about 100, preferably from about 0 to about 80, more preferably from about 0 to about 60, more preferably from about 0 to about 40, even more preferably from about 0 to about 20; and/or c) a color grade of from about 1 to about 10, preferably from about 1 to about 8, more preferably from about 1 to about 6, as graded on the Gardner Color standard number scale; the treatment composition further comprising one or more benefit agents.

I. The treatment composition according to paragraph H, wherein the plant rosin material comprises a plant rosin ester material.

J. The treatment composition according to any of paragraphs A-I, wherein the plant rosin material is characterized by a softening point of from about 60° C. to about 100° C., and by an acid number of from about 0 to about 80, more preferably an acid number of from about 0 to about 60.

K. The treatment composition according to any of paragraphs A-J, wherein the plant rosin material is at least partially hydrogenated.

L. The treatment composition according to any of paragraphs A-K, wherein the plant rosin material comprises a material selected from the group consisting of gum rosin, wood rosin, tall oil rosin, derivatives thereof, and mixtures thereof, preferably gum rosin, derivatives thereof, and mixtures thereof, more preferably a gum rosin ester.

M. The treatment composition according to any of paragraphs A-L, wherein the plant rosin material and the one or more benefit agents are present in a weight ratio of from about 5:95 to about 95:5, preferably from about 20:80 to about 80:20, more preferably from about 30:70 to about 70:30, more preferably from about 40:60 to about 60:40.

N. The treatment composition according to any of paragraphs A-M, wherein the one or more benefit agents is selected from the group consisting of fragrance material, silicone oils, waxes, hydrocarbons, higher fatty acids, essential oils, lipids, skin coolants, vitamins, sunscreens, antioxidants, glycerine, malodor reducing agents, odor-controlling materials, antistatic agents, softening agents, insect and moth repelling agents, colorants, optical brighteners, whiteness enhancers, defoamers, anti-foaming agents, UV protection agents for fabrics and skin, sun fade inhibitors, anti-allergenic agents, water proofing agents, skin care agents, glycerin, natural actives, aloe vera, vitamin E, shea butter, cocoa butter, brighteners, antiperspirant actives, emollients, skin sensates, and mixtures thereof, preferably selected from fragrance material.

O. The treatment composition according to any of paragraphs A-N, wherein the treatment composition comprises particles, wherein the particles comprise the plant rosin material and the one or more benefit agents.

P. The treatment composition according to any of paragraphs A-O, wherein the treatment composition further comprises an adjunct ingredient, wherein the adjunct ingredient is selected from an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, a perfume delivery system, structure elasticizing agents, fabric softening agents, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof.

Q. The treatment composition according to any of paragraphs A-P, wherein the adjunct ingredient comprises a surfactant system, fabric softening agents, or combinations thereof, preferably wherein the surfactant system comprises anionic surfactant, nonionic surfactant, cationic surfactant, and/or zwitterionic surfactant, and/or preferably wherein the fabric softening agents comprise a quaternary ammonium compound, silicone compounds, or both.

R. The treatment composition according to any of paragraphs A-Q, wherein the treatment composition further comprises an amphiphilic polymer, preferably an amphiphilic graft co-polymer, more preferably an amphiphilic graft co-polymer comprising a polyalkylene glycol as a graft base and one or more side chains, the side chains comprising vinyl acetate moieties and optional N-vinylcaprolactam moieties.

S. The treatment composition according to any of paragraphs A-R, wherein the treatment composition is a liquid.

T. The treatment composition according to any of paragraphs A-S, wherein the treatment composition is a consumer product composition, preferably a fabric care composition, a hard surface cleaner composition, a dish care composition, a hair care composition, a body cleansing composition, or a mixture thereof, preferably wherein the fabric care composition is a fabric detergent composition, a fabric conditioning composition, or a mixture thereof.

U. A method of treating a surface, preferably a fabric, the method comprising the step of contacting the surface with the treatment composition according to any of paragraphs A-T, optionally in the presence of water.

Test Methods

It is understood that the test methods that are disclosed in the Test Methods Section of the present application should be used to determine the respective values of the parameters of Applicant's claimed subject matter as claimed and described herein.

Test Method for Determining the Logarithm of the Octanol/Water Partition Coefficient (log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Softening Point Test Method

If available, the softening point of a plant rosin material as provided by the manufacturer/supplier is to be used.

If not available from the manufacturer/supplier, the softening point is determined according to ASTM E28-18, "Standard Test Methods for Softening Point of Resins Derived from Pine Chemicals," using the version approved Jul. 1, 2018, and published July 2018. More specifically, the Reference Method ("Automated Ring and Ball Softening Point Method") provided therein is to be followed. The method is summarized here.

As used herein (and as described in ASTM E28-18), the softening point is defined as the temperature at which a disk of the sample held with a horizontal ring (brass shouldered ring; 19.8 mm inner ring diameter, 23.0 outer diameter, as indicated in the ASTM method) is forced downward a distance of 25.4 mm (1 in.) under the weight of a steel ball (9.53 mm diameter; mass between 3.45 and 3.55 g) as the sample is heated at 5 C/min in a water, glycerin, silicone oil, ethylene glycol/water, or glycerin/water bath.

Sample Preparation: Select a representative sample of the rosin material to be tested. The sample should include flakes, pastilles, or freshly broken lumps free of oxidized surfaces; avoid inclusion of finely divided material or dust. Melt the sample in a clean container; avoid overheating, and avoid incorporating air bubbles into the sample. The time from the beginning of heating to the pouring of the sample should not exceed 15 minutes. Rest the ring, bottom down, on a metal surface; the ring may be preheated. Pour the melted rosin sample into the ring so as to leave an excess upon cooling. After cooling for at least 30 minutes, remove excess material from the periphery and top of the ring.

Bath Liquid: The selection of the bath liquid will depend on the softening point ("SP") of the rosin material. For SPs between 35 C and 80 C, use water (distilled or deionized, freshly boiled). For SPs between 80 C and 150 C, use USP Glycerin. For SPs above 80 C, use Silicone Oil (Polydimethylsiloxane—200 fluid, 50 cSt, from Dow Corning, Midland, MI). For SPs up to 35 C, use a 50/50 (v/v) mixture of Ethylene Glycol and Distilled Water; the bath should be cooled to −25 C in a precooled freezer or an isopropyl dry-ice bath.

Test: Use a suitable automated ring and ball-softening point instrument with control unit; calibrate according to the manufacturer's instructions. Provide a stir bar to a 600 mL beaker and fill with a bath liquid as provided above, depending on the softening point of the rosin material. Set up the apparatus, ring, ball, test insert, support pins as recommended by the manufacturer's instructions. Verify that the control unit is set for the correct bath liquid.

Heat the bath so that the temperature of the bath liquid is raised uniformly at a rate of 5 C/min. The test is complete when then light beam has been interrupted by the falling ball and material. Record the softening point at the temperature displayed on the unit after the test is completed.

Acid Number Test Method

If available, the acid number of a plant rosin material as provided by the manufacturer/supplier is to be used.

If not available from the manufacturer/supplier, the acid value is determined according to ASTM D465-15 (Reapproved 2020), "Standard Test Methods for Acid Number of Pine Chemical Products Including Tall Oil and Other Related Products," as approved Jun. 1, 2020 and published June, 2020. More specifically, the Referee Method ("Potentiometric Method") provided therein is to be followed. The method is summarized here.

Provide freshly chipped samples of rosin material, which may be further crushed to facilitate weighing and dissolution; pieces with oxidized surfaces, as well as existing rosin dust or powder, should not be used. If a nonhomogenous liquid, place in a closed container with a capillary vent or its equivalent, and heat in a hot water bath; the sample may be agitated during heat, and used after homogenous and well stirred.

Based on the following table, transfer the proscribed amount of sample to a 400 mL tall-form beaker; add the proper amount of solvent I and swirl to dissolve, heating gently if necessary. Add the proper amount of solvent II, if required, and cool to near room temperature. Immerse each electrode of a glass electrode pH meter (calibrated/standardized according to the manufacturer's instructions) in the solution. Stir with a stir bar.

Titrate with a standard alkali solution (a 0.5 N or 0.1 N KOH solution), recording the buret and pH meter readings. Sufficient alkali may be added to bring the pH of the solution to about 8. Add alkali in 1.0 mL portions until the change in pH per increment added amounts to about 0.3 pH unit. Reduct the additions of alkali to 0.1 mL or smaller until the end point has been passed, as indicated by a significant decrease in pH units er 0.1 mL added. Continue the titration with 1.0 mL portions until it becomes apparent that the inflection point has been well defined.

Determine the inflection point (point of maximum change in pH per mL of alkali solution) to the nearest 0.05 mL by plotting the pH readings against the milliliters of alkali used. (For greater accuracy, the chance in pH per mL may be plotted against the pH; the peak corresponds to the inflection point.) The inflection point is considered the end point of the titration.

The acid number of the sample, expressed as milligrams of KOH per gram of sample is calculated as follows, and may be reported to the nearest whole number:

$$\text{Acid Number} = (A \times N \times 56.1)/B$$

where: A=alkali solution (in mL) required for titration of the specimen; N=normality of the alkali solution, and B=specimen weight (in grams).

Color Grade Test Method (Gardner Color)

If available, the color grade (Gardner color) of a plant rosin as provided by the manufacturer/supplier is to be used.

If not available from the manufacturer/supplier, the color grade (Gardner color) is determined according to ASTM D6166-12 (Reapproved 2016), "Standard Test Method for Color of Pine Chemicals and Related Products (Instrumental Determination of Gardner Color)," as approved Dec. 1, 2016, and published December, 2016. The method is summarized here.

The color of a liquid sample is measured using an instrument, such as a Gardner Color Comparator L, 115V (ex. BYK), capable of measuring transmitted color and reporting in Gardner colors (or, less preferred, in a color system that can be converted to Gardner colors by known methods, such as those disclosed in the ASTM D6166-12). The instrument is calibrated according to the manufacturer's instructions.

To prepare the rosin sample for color analysis, a molten sample of the rosin material is introduced to a glass cuvet (10-mm path, unless a different path length is specified by the instrument manufacturer). If the sample is solid, it should comprise freshly broken lumps and be free of dust and finely divided material; the solid should be melted (e.g. in 15 minutes or less, in an oven, sand bath, or oil bath), taking care to avoid overheating and introduction of bubbles. After the molten sample is introduced to the glass cuvet, measurements should be taken while still molten. If the material is cloudy, it should be filtered.

The glass cuvet is inserted into the instrument, and the color is measured by following the manufacturer's instructions.

Flash Point Test Method

If available, the flash point of a plant rosin as provided by the manufacturer/supplier is to be used.

If not available from the manufacturer/supplier, the flash point is determined according to ASTM D92-18, "Standard Test Methods for Flash and Fire Points by Cleveland Open Cup Tester," as approved Jul. 1, 2018, and published July, 2018.

Test Method for Determining Amounts of Major Rosin Acid Isomers

If available, the amounts of the major rosin acid isomers of a plant rosin as provided by the manufacturer/supplier is to be used.

If not available from the manufacturer/supplier, the amounts of the major rosin acid isomers are determined according to ASTM D5974-15, "Standard Test Method for Fatty and Rosin Acids in Tall Oil Fractionation Products by Capillary Gas Chromatography," as approved Jul. 1, 2015, and published August, 2015. The method is summarized here.

This method uses gas chromatography to determine the levels of, for example, rosin acids present in a rosin sample. Prior to chromatographic separation, certain free acids should be converted to more volatile and more stable methyl esters. For rosin acids, this conversion may take place by means of tetramethylammonium hydroxide (TMAH).

To prepare the methyl ester, a rosin sample (if solid, freshly broken to avoid oxidation) is dissolved in 0.5-3.0 mL of a 50:50 ether/methanol mixture (and optionally 2 to 3 drops of toluene), 2 to 3 drops of phenolphthalein indicator solution is added. The mixture is titrated to a pH of 7.9 to 8.1, or to the very first permanent pink color, with a 6% solution of TMAH. If over-titrated, the mixture may be back-titrated with a 5% acetic acid solution (v/v) in methanol. When the solution is injected into the heated injection port of the chromatograph, the tetramethylammonium salts are pyrolyzed to methyl esters.

A gas chromatograph (GC) equipped with a flame ionization detector (FID) is used and operated under the following conditions: Column temperature (oven temperature)—initial, 150 C; hold, 5 min.; ramp, 5 C/min; final 250 C; hold 10 min; injection port temp., 300 C; injection port liner, glass split; detector temp., 325 C; carrier gas, helium; linear gas velocity, 19.5-20.5 cm/s; split ratio, 100 to 1 maximum; detector, FID; hydrogen, 30 mL/min; air, 400 mL/min; makeup gas, 30 mL/min. A high resolution column, preferably 30 m in length, 0.32 mm internal diameter, with a 0.20-μm film thickness of bicyanopropylsiloxane-type liquid, is used.

Prepare calibration standards of myristic acid and high-purity standards of rosin acids that are expected to be present, record the weights, and convert to methyl esters as described above. To prepare the test sample, accurately weigh about 50 mg of sample and about 15 mg of myristic acid in a suitable vial, record the weight, and convert to methyl esters as described above.

Use the calibration standards (injecting 0.5-1.0 μL) to calibrate the GC, recording the retention times and calculating the individual relative response factors. To analyze the test sample, inject 0.5-1.0 μL (diluting the sample with additional solvent if necessary), obtain the peak areas of all of the peaks needed from the chromatogram, and calculate the absolute value of each peak of interest. The relative percent of each rosin acid methyl ester present may be determined by dividing the peak area for the rosin acid methyl ester being determined by the sum of areas of all rosin acid methyl ester peaks.

Fabric Treatment Method

When treating fabrics with a composition according to the present disclosure in the experiments below, the following method is followed unless otherwise indicated. For each treatment, a washing machine (ex Miele) is loaded with about 3 kg of a fabric load. The fabric load comprises about 1065 g knitted cotton fabric and about 1065 g polyester-cotton fabrics (50/50). Additionally, the fabric load comprises twenty terry towel tracers, which weigh together about 870 g. Then one washing cycle is run at 95° C.

Prior to the test treatment, the load is preconditioned twice, each time using the 95° C. short cotton cycle with 79 g of unperfumed IEC A Base detergent (ex WFK Testgewebe GmbH), followed by two additional 95° C. washes without detergent.

For the test treatment, the load is washed using a 40° C. short cotton cycle, 1200 rpm spin speed with 79 g IEC A Base detergent, which is added at the start of the wash cycle in the appropriate dispenser. A dosage of 40 ml of the test fabric treatment composition is added in the appropriate dispenser.

Method to Determine Headspace Concentration Above Treated Fabrics

The fabric tracers from the abovementioned Fabric Treatment method may be analyzed via headspace analysis at at least two specific touchpoints:
- WFO (Wet Fabric Odor, or WET): Wet fabrics are analyzed after the fabric treatment method is finished.
- DFO (Dry Fabric Odor, or DRY): Dried Fabrics are analyzed after the fabrics have been line-dried in a closed room for approximately twenty-four hours.

The headspace above the cotton terry tracers is analyzed using SPME headspace GC/MS (gas chromatography mass spectrometry) approach. 4 cm×4 cm aliquots of cotton tracers are transferred to 25 ml headspace vials. The fabric samples are equilibrated for 10 minutes at 65° C. The headspace above the fabrics is sampled via SPME (50/30 μm DVB/Carboxen/PDMS) for 5 minutes. The SPME fiber is subsequently on-line thermally desorbed into the GC. The analytes are analyzed by GC/MS in full scan mode. The total perfume HS response and perfume headspace composition above the tested legs can be determined.

Viscosity Method

Viscosity of a liquid composition is measured using a DV-E viscometer from Brookfield. The spindle is automatically spun at a rate of 60 rpm until a stable value is given in centipoise (cP).

Viscosity of the premix comprising rosin plant, delivery agent and potentially emulsifying agent is measured using a HAAKE MARS from Thermo Scientific using a 60 mm 1° Cone and a gap size of 52 micrometers. The shear viscosity at $20\ s^{-1}$ can be obtained from a logarithmic shear rate sweep from $0.01\ s^{-1}$ to $1200\ s^{-1}$ at 21° C. The viscosity may be expressed as centipoise (cP).

Particle Size Determination

Depending on the relative size of the particle, one of two methods is employed: image analysis if the approximate volume-weighted median particle size of the population is 10 μm or greater, or microscopy if the approximate volume-weighted median particle size of the population is less than 10 μm. These methods are described in more detail below.

A. Image Analysis

The volume-weighted median particle size is calculated from images taken from the sample flowing through a variable size flow cell. This instrument is specifically designed for image analysis device for liquid applications (Occhio FC200S). The sample is pumped via a syringe pump at very low speed through the flow cell, while the sample passes through the flow cell images are taken at set times. The speed is matched with the frame speed of the camera and it is dependent on the behaviour of the sample and the particles it contains. The flow cell sizes used were 250 and 500 μm and were depending on the size of the capsules. Detection of the capsules is done via grayscale threshold. Callisto version 2013.13 software is used to read out the pixels and calculate size and shape parameters. The size descriptor used is ISO area diameter.

Illumination is a red-led light source, adjustment of illumination is done manually until proper grayscale detection of the particles is possible. Hardware magnification is dependent on the size of the particles: 6× or 9×.

B. Microscopy

The volume-weighted median particle size of the particles is calculated from the values obtained by microscopically observing and measuring the diameter of around 900 capsules observed in randomly sampled aliquots. The microscope used is the Leica DM6000B. The magnification of the microscope is set to 200×. The outputs obtained after the microscopy analysis are: (1) list of diameters detected; and (2) counts per each diameter size detected.

Therefore, the volume (V) of each particle is calculated with the following equation:

$$V = \frac{4}{3}\pi r^3$$

where r is the radius of each detected particle. Finally, the volume-weighted median particle size is calculated (e.g., via a spreadsheet, such those created in Microsoft Excel™), assuming that each particle is a sphere.

EXAMPLES

The examples provided below are intended to be illustrative in nature and are not intended to be limiting.

Example 1. Exemplary Plant Rosin Materials

Table 1 shows a variety of commercially available plant rosin materials. Additional information is provided where available. For treatment compositions according to the present disclosure, rosin materials according to Nos. 2, 4, 7, and 9 may be particularly preferred.

TABLE 1

| No. | Rosin Type | Type | Derivative Additives | Softening Point (° C.) | Acid Value (mg KOH/g) | TRADE NAME | Mfr.* |
|---|---|---|---|---|---|---|---|
| 1 | Gum Rosin | — | — | 79 | 163 | — | C |
| 2 | Gum Rosin | Glycerol ester | — | 88 | 8 | Permalyn 5095 | A |
| 3 | Gum Rosin | Pentaerythritol ester | — | 125 | 13 | Lurefor 125 | C |
| 4 | Gum Rosin | Pentaerythritol ester | — | 100 | 15 | Permalyn 5110 | A |
| 5 | Gum Rosin | Methyl ester | — | — | 5 | Abalyn D-E | A |
| 6 | Gum Rosin | Hydrogenated | — | 70 | 158 | Staybelite Resin-E | A |
| 7 | Misc. Rosin | Partially Hydrogenated | — | 75 | 168 | Foralyn E | A |
| 8 | Gum Rosin | Partially dimerized | — | 103 | 146 | Poly-Pale | B |
| 9 | Wood Rosin | Hydrogenated glycerol ester | — | 84 | 6 | Foral 85 | B |
| 10 | Wood Rosin | Hydrogenated pentaerythritol ester | — | 99 | 11 | Foral 105 | B |
| 11 | Tall Oil | Saponified sodium soap | — | — | 0.5 | Dresinate TX Rosin Soap | A |
| 12 | Misc. Rosin | Dimerized; Zinc resinate | Zinc salt | 160 | 5 | Zincogral Z | B |
| 13 | Wood Rosin | Pentaerythritol ester | Maleic-Modified | 132 | 140 | Pentalyn- FC | B |
| 14 | Gum Rosin | Dimerized | — | 144 | 145 | Dymerex | A |
| 15 | Rosin acids | Dimerized | — | 138 | 154 | Polygral 140 | B |
| 16 | Wood Rosin | Hydrogenated | — | 67 | 165 | Foral AX | B |
| 17 | Gum Rosin | Glycerol ester | — | 84 | 6.4 | Ester Gum 8L-M | A |
| 18 | Rosin | Polimerized | Maleic-Modified | 130 | 10 | Dertoline MG 130 | B |
| 19 | Rosin | Pentaerythritol ester | — | 128 | 12 | Dertopoline 125 | B |
| 20 | Gum Rosin | Pentaerythritol ester | | 101 | 13 | Permalyn 6110 | A |

*Mfr. = Manufacturer, according to the following key:

A - Eastman

B - DRT

C Luresa Resinas S.L.

Example 2. Freshness Benefits

A liquid fabric enhancer (LFE) base composition according to Table 2A, below, is provided.

TABLE 2A

| Ingredient (wt %) | Composition |
|---|---|
| Softening active[1] | 7.00% |
| Formic acid | 0.045% |
| Sodium hydroxyethane diphosphonic acid | 0.0071% |
| Silicone antifoam | 0.002% |
| Structuring agent[2] | 0.2% |
| Water | Balance to 100% |

[1]Diester quaternary ammonium compound (Ci-DEEDMAC=Ditallowoyl Ethoxy Ester Dimethyl Ammonium Chloride [MDEA based, Methyl Di-Ethanol amine based quat, available from Evonik])
[2]FLOSOFT ™ FS 222 (ex SNF Floerger ®)

The following rosin/perfume premixes are prepared as shown in the below table. The weight percentages are based on weight of the premix composition.

TABLE 2B

| Premix # | Plant Rosin Material Trade Name | Wt % | Benefit Agent Type | Wt % |
|---|---|---|---|---|
| 1 | Permalyn 5095 | 70% | Perfume | 30% |
| 2 | Permalyn 5110 | 70% | Perfume | 30% |
| 3 | Abalyn D-E | 70% | Perfume | 30% |

Various liquid fabric enhancer ("LFE") products are made with the premixes of Table 2B ("perfume+plant rosin"). For each leg, a parallel product is made that only adds the perfume (no premix; no plant rosin material; "perfume only").

The products are used to treat fabrics according to the method provided above, and the dry fabric odor (DFO) for each is measured. The results are provided in Table 2C. Additionally, the Table 2C shows the "Delta DFO," showing the difference between the DFO scores for the products that include the premixes of Table 2B and the products that only include the perfume. Furthermore, the "DFO Ratio" is the ratio of the two DFO scores in that leg.

TABLE 2C

| Leg | Premix included in LFE | Plant Rosin Material Trade Name | Plant Rosin Material classification | DFO Headspace (nM/L) (perfume + plant rosin) | DFO Headspace (nM/L) (perfume only) | Delta DFO | DFO Ratio | Dispersibility (1-10)[2] |
|---|---|---|---|---|---|---|---|---|
| A | 1 | Permalyn 5095 | Glycerol ester of Gum Rosin | 60.2 | 6.12 | +54.08 | 9.8 | 4 |
| B | 2 | Permalyn 5110 | Pentaerythritol ester of Gum Rosin | 149.0 | 4.61 | +144.39 | 32.3 | 6 |
| C | 3 | Abalyn D-E | Methyl ester of Gum Rosin | 2.57 | 0.33 | +2.24 | 7.8 | 3 |

[2]Dispersibility is relative to the ease of dispersing rosin material in the finished product formulation, where 10 = very difficult to disperse, 5 = average dispersibility, and 1 = good dispersibility.

Relatively higher Delta DFO scores and DFO Ratios indicate that the formulation comprising the premix is providing freshness benefit compared to perfume-only formulation.

As seen in the results for Legs A, B and C, LFE formulations that include plant rosin material all provide DFO freshness benefits (as indicated by Delta DFO and DFO ratio) compared to the respective perfume-only formulations. That being said, it can be seen the plant rosin glycerol esters and pentaerythritol esters result in relatively higher DFO scores compared to the plant rosin methyl esters. Pentaerythritol esters provide better DFO scores; however, such materials can be relatively more challenging to process, as shown by the dispersibility scores. Thus, the formulator can select a plant rosin material that best aligns with the desired performance and processability parameters, with glycerol esters providing a preferred combination of performance and dispersibility aspects.

Example 3. Acid Number and Softening Point

Various plant rosin materials are added to a liquid fabric enhancer base to make a finished product. The formulation of the LFE composition is reported in Table 3A:

TABLE 3A

| Ingredient (wt %) | Composition |
|---|---|
| Softening active[1] | 7.00% |
| Formic acid | 0.045% |
| Sodium hydroxyethane diphosphonic acid | 0.0071% |
| Silicone antifoam | 0.002% |
| Plant Rosin Material | 1.0% |
| Water | Balance to 100% |

[1]Diester quaternary ammonium compound (Ci-DEEDMAC=Ditallowoyl Ethoxy Ester Dimethyl Ammonium Chloride [MDEA based, Methyl Di-Ethanol amine based quat, available from Evonik])

Table 3B shows a list of certain plant rosin materials, each of which has an acid number higher than 140 (measured in mg KOH/g). Dispersibility of the rosin material in the LFE composition is assessed and reported below.

The plant rosin materials listed in Table 3B are relatively difficult to disperse in the finished product formulation, as indicated by relatively high dispersibility ratings. This appears to be the case even when the softening point is relatively low (see, e.g., Legs 3A-6 and 3A-7).

TABLE 3B

| Leg | Trade Name | Softening point [° C.] | Acid number [mg KOH/g] | Dispersibility (1-10)[2] |
|---|---|---|---|---|
| 3B-1 | Pentalyn-FC | 132 | 140 | 7 |
| 3B-2 | Dymerex | 144 | 145 | 7 |

TABLE 3B-continued

| Leg | Trade Name | Softening point [° C.] | Acid number [mg KOH/g] | Dispersibility (1-10) [2] |
|---|---|---|---|---|
| 3B-3 | Poly-Pale | 103 | 146 | 7 |
| 3B-4 | Polygral 140 | 138 | 154 | 7 |
| 3B-5 | Gum Rosin | 80 | 163 | 6 |
| 3B-6 | Foral AX | 67 | 165 | 10 |
| 3B-7 | Foralyn E | 75 | 168 | 8 |

[2] Dispersibility is relative to the ease of dispersing the rosin material in the finished product formulation, where 10 = very difficult to disperse, 5 = average dispersibility, and 1 = good dispersibility.

Even when a plant rosin material has a relatively high acid number, it may still be a useful material in treatment compositions. For example, it has been found that when a material, such as Foralyn E (see Leg 3A-7 above) has a relatively high acid number and relatively low softening point, it may still give good freshness results. With regard to Foralyn E, it is believed that this is because the material is at least partially hydrogenated. Therefore, it is believed that selecting a plant rosin material with a high acid value, a low softening point, and at least partial hydrogenation can provide a useful treatment composition.

Table 3C shows a list of certain plant rosin materials, each of which has an acid value lower than 15 (measured in mg KOH/g).

TABLE 3C

| Leg | Trade Name | Softening point [° C.] | Acid number [mg KOH/g] | Dispersibility (1-10) [2] |
|---|---|---|---|---|
| 3C-1 | Zincogral Z | 160 | 5 | 7 |
| 3C-2 | Foral 85 | 84 | 6 | 4 |
| 3C-3 | Ester Gum 8L-M | 84 | 6.4 | 4 |
| 3C-4 | Permalyn 5095 | 88 | 8 | 4 |
| 3C-5 | Dertoline MG 130 | 130 | 10 | 6 |
| 3C-6 | Foral 105 | 99 | 11 | 5 |
| 3C-7 | Dertopoline 125 | 128 | 12 | 6 |
| 3C-8 | Permalyn 6110 | 101 | 13 | 5 |
| 3C-9 | Lurefor 125 | 125 | 13 | 6 |

[2] Dispersibility is relative to the ease of dispersing the rosin material in the finished product formulation, where 10 = very difficult to disperse, 5 = average dispersibility, and 1 = good dispersibility.

When the acid number is relatively low, the differences in dispersibility ratings can be explained by the differences in softening point. In sum, dispersibility improves when the softening point of the plant rosin material is relatively lower.

The confirmation of the statistical influence of the softening point on the dispersibility of rosin materials with an acid value lower than 15 (mg KOH/g) is confirmed by FIG. 1. In FIG. 1, the dispersibility ratings are plotted vs. the softening point. The correlation of softening point vs dispersibility is statistically significant as confirmed by the $R^2$ (0.967) and pvalue (<0.001). The correlation shows how, when the acid number is relatively low, low softening points may be preferred for the dispersibility of the rosin material in the finished product.

Example 4. Number of Ester Groups

Table 4 compares esters of similar gum rosins. The materials are made into rosin/perfume premixes (in a 50:50 weight ratio), which are assessed for premix viscosity. The premixes are then incorporated into base liquid fabric enhancer base compositions and assessed for dispersibility. Results are shown in in Table 4.

TABLE 4

| Leg | Trade Name | Plant Rosin Material classification | Ester groups per mole of plant rosin ester material | Softening point [° C.] | Premix Viscosity [3] | Dispersibility of Premix (1-10) [2] |
|---|---|---|---|---|---|---|
| 4-1 | Permalyn 5095 | Glycerol ester of Gum Rosin | 3 | 88 | 0.7753 | 4 |
| 4-2 | Permalyn 5110 | Pentaelythritol ester of Gum Rosin | 4 | 100 | 1.314 | 6 |

[2] Dispersibility is relative to the ease of dispersing the premix rosin/perfume in the finished product formulation, where 10 = very difficult to disperse, 5 = average dispersibility, and 1 = good dispersibility.
[3] Viscosity at 20° C. and shear rate 11.71 s$^{-1}$ As shown in Table 4, increasing the number of ester groups per mole of plant rosin ester material correlates with increased Softening Point of the rosin material. In parallel, the increase in ester groups per mole correlates with increasing the viscosity of the rosin when mixed together with perfume. Furthermore, increasing the ester groups per mole from three to four results in decreased dispersibility in the finished product.

Example 5. Color Gradings

Table 5 shows a list of plant rosin materials having different Color Grades. The color grade of a plant rosin material is determined according to the Gardner color scale as described in the Test Method section above.

TABLE 5

| No. | Rosin Type | Derivative Type | Additives | Color Grade[1] | TRADE NAME | Mfr.* |
|---|---|---|---|---|---|---|
| 1 | Gum Rosin | Pentaerythritol ester | — | <1 | Permalyn 6110 | A |
| 2 | Gum Rosin | Glycerol ester | — | 3 | Permalyn 5095 | A |
| 3 | Wood Rosin | Hydrogenated glycerol ester | — | 3 | Foral 85 | B |
| 4 | Gum Rosin | Glycerol ester | — | 3.8 | Ester Gum 8L-M | A |
| 5 | Wood Rosin | Pentaerythritol ester | Maleic-Modified - | 4 | Pentalyn- FC | B |
| 6 | Wood Rosin | Hydrogenated pentaerythritol ester | — | 5 | Foral 105 | B |
| 7 | Gum Rosin | Pentaerythritol ester | — | 6 | Lurefor 125 | A |
| 8 | Gum Rosin | — | — | 6+ | Gum Rosin | C |
| 9 | Gum Rosin | Partially dimerized | — | 8 | Poly-Pale | A |
| 10 | Rosin acids | Dimerized | — | 9 | Polygral 140 | B |
| 11 | Misc. Rosin | Dimerized; Zinc resinate | Zinc salt | 12 | Zincogral Z | B |

[1]Color Grade is assessed according to the Gardner color scale as described in the Test Method section above, where 1 = light color, 18 = very dark color
*Mfr. = Manufacturer, according to the following key: A = Eastman; B = DRT; C = Luresa Resinas S.L.

Typically, lower values of Color Grade are preferred so to have minimal effect on the final color of the treatment composition. By way of example, attention is directed to FIG. 1, which shows color photographs of liquid fabric enhancer (LFE) products that include the plant resin materials provided in Table 5. The LFE products are formulated with, among other things, perfume and 7 wt % of an ester quat fabric softening agent and stored for two days at 25° C.). After the storage period, photographs are taken of resulting composition to show color changes that occur over time.

As can be seen in the table of FIG. 1, plant rosin materials having a relatively lower color grade tend to result in less discoloration of the LFE product upon storage. For example, compare the relative colors of the LFE products formulated with Resins 1-4 (lighter) vs. those formulated with Resins 8-11 (darker). This selection of plant rosin materials having a relatively low color grade may be particularly important when formulating/manufacturing an uncolored, undyed, or lightly colored product composition. Such selections may be preferred even when formulating or manufacturing a dyed or colored product, as the color change can have a detrimental effect on the aesthetics of the product. For example, when formulating a blue-colored product, the less-desirable rosin's yellowish color upon aging may result in a product color change towards green.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A treatment composition comprising a plant rosin material and one or more benefit agents,
   wherein the plant rosin material is a plant rosin ester material,
      wherein the plant rosin ester material comprises, on average, from about two to about six moles of ester groups per mole of plant rosin ester material, and
      wherein the plant rosin material comprises a gum rosin ester; and
   wherein the one or more benefit agents comprises fragrance material.

2. The treatment composition according to claim 1, wherein the plant rosin ester material is derived from a plant rosin and an alcohol,
   wherein the alcohol comprises from two to six carbon atoms.

3. The treatment composition according to claim 2, wherein the alcohol from which the plant rosin ester material is derived is selected from the group consisting of glycerol, pentaerythritol, and mixtures thereof.

4. The treatment composition according to claim 3, wherein the alcohol from which the plant rosin ester material is derived is glycerol.

5. The treatment composition according to claim 1, wherein the plant rosin ester material is characterized by one or more of the following:
   a) a softening point of from about 50° C. to about 120° C.; and/or
   b) an acid number of from 0 to about 100; and/or
   c) a color grade of from about 1 to about 10, as graded on the Gardner Color standard number.

6. The treatment composition according to claim 5, wherein the plant rosin ester material is characterized by one or more of the following:
   a) a softening point of from about 60° C. to about 100° C.; and/or
   b) an acid number of from 0 to about 20; and/or
   c) a color grade of from about 1 to about 6, as graded on the Gardner Color standard number.

7. The treatment composition according to claim 1, wherein the plant rosin material is characterized by a softening point of from about 60° C. to about 100° C., and by an acid number of from 0 to about 80.

8. The treatment composition according to claim 1, wherein the plant rosin material is at least partially hydrogenated.

9. The treatment composition according to claim 1, wherein the plant rosin material additionally comprises a material selected from the group consisting of wood rosin, tall oil rosin, derivatives thereof, and mixtures thereof.

10. The treatment composition according to claim 1, wherein the plant rosin material and the one or more benefit agents are present in a weight ratio of from about 5:95 to about 95:5.

11. The treatment composition according to claim 1, wherein the one or more benefit agents further comprises a material selected from the group consisting of silicone oils, waxes, hydrocarbons, higher fatty acids, essential oils, lipids, skin coolants, vitamins, sunscreens, antioxidants, glycerine, malodor reducing agents, odor-controlling materials, antistatic agents, softening agents, insect and moth repelling agents, colorants, optical brighteners, whiteness enhancers, defoamers, anti-foaming agents, UV protection agents for fabrics and skin, sun fade inhibitors, anti-allergenic agents, water proofing agents, skin care agents, natural actives, aloe vera, vitamin E, shea butter, cocoa butter, brighteners, antiperspirant actives, emollients, skin sensates, and mixtures thereof.

12. The treatment composition according to claim 1, wherein the treatment composition comprises particles,
wherein the particles comprise the plant rosin material and the fragrance material.

13. The treatment composition according to claim 1, wherein the treatment composition further comprises an adjunct ingredient,
wherein the adjunct ingredient is selected from an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, a perfume delivery system, structure elasticizing agents, fabric softening agents, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof.

14. The treatment composition according to claim 13, wherein the adjunct ingredient comprises a surfactant system, fabric softening agents, or combinations thereof.

15. The treatment composition according to claim 1, wherein the treatment composition further comprises an amphiphilic polymer.

16. The treatment composition according to claim 1, wherein the treatment composition is a liquid.

17. The treatment composition according to claim 1, wherein the treatment composition is a fabric care composition, a hard surface cleaner composition, a dish care composition, a hair care composition, a body cleansing composition, or a mixture thereof.

18. The treatment composition according to claim 1, wherein the treatment composition is a fabric care composition.

19. The treatment composition according to claim 1, wherein the treatment composition is a fabric care composition, wherein the fabric care composition is a fabric conditioning composition.

20. A method of treating a surface, the method comprising the step of contacting the surface with the treatment composition according to claim 1, optionally in the presence of water.

21. A treatment composition comprising:
a plant rosin material,
wherein the plant rosin material comprises a gum rosin ester, and
wherein the plant rosin material is characterized by at least one of the following characteristics:
a) a softening point of from about 50° C. to about 120° C.;
b) an acid number of from 0 to about 100; and/or
c) a color grade of from about 1 to about 10, as graded on the Gardner Color standard number scale;
the treatment composition further comprising one or more benefit agents,
wherein the one or more benefit agents comprises fragrance material.

* * * * *